United States Patent [19]

Goldstein

[11] Patent Number: 4,469,108

[45] Date of Patent: Sep. 4, 1984

[54] DEVICE FOR MEASURING PENILE TUMESCENCE AND RIGIDITY

[75] Inventor: Abraham M. B. Goldstein, Los Angeles, Calif.

[73] Assignee: University of Southern California, Los Angeles, Calif.

[21] Appl. No.: 405,134

[22] Filed: Aug. 4, 1982

[51] Int. Cl.³ ............................................. A61B 5/00
[52] U.S. Cl. ..................................... 128/694; 128/774
[58] Field of Search ............... 128/87 R, 87 A, 132, 128/774, 138 R, 138 A

[56] References Cited

U.S. PATENT DOCUMENTS 4,103,678  8/1978  Karacan et al. ................... 128/774
4,174,709 11/1979  Maddux .......................... 128/87 R X

OTHER PUBLICATIONS

Senemlow, J. L. et al., "Sexual Instrumentation", IEEE BME Transactions vol. BME-30, No. 6 Jun. 1983 pp. 309-319.

Barry, J. M. et al., "NPT Monitoring with Stamps", Urology Feb. 1980 vol. 15 No. 2 pp. 171-172.
Zimmer, "Fuiger Extension Splint", Aug. 1947 Fracture Appliance Catalog.
"Erectionster" Walter Koss OHG, D-6222 Geisenheim/Rhein (Germany).

Primary Examiner—Edward M. Coven
Assistant Examiner—Francis J. Jaworski
Attorney, Agent, or Firm—Nilsson, Robbins, Dalgarn, Berliner, Carson & Wurst

[57] ABSTRACT

A device for measuring tumescence and rigidity of the penis during erection has a first portion receivable about the base of the penis and actuable from an initial condition to an expanded condition by tumescence of the penis, and a second portion mountable to the penis at a location remote from the base for movement with the outer end of the penis. In a preferred embodiment, the first portion is constructed to restrict its return to the initial condition, and the first and second portions are connected to restrict movement of the second portion toward the first portion.

19 Claims, 6 Drawing Figures

DEVICE FOR MEASURING PENILE TUMESCENCE AND RIGIDITY

BACKGROUND OF THE INVENTION

This invention relates to the medical diagnosis of sexual impotence and, more particularly, to a device for measuring tumescence and rigidity of the penis during nocturnal erection.

In treating sexual impotence, one must initially determine whether the impotence is organic or psychogenic in origin. This determination is often difficult to make because a variety of inhibitions can cancel out sexual stimuli, making it appear as though the patient has an organic disorder when none exists. However, most men, even those suffering from psychogenic impotence, experience spontaneous erections in their sleep. The only known exception is when the person suffers from an organic disorder which prevents erection.

A number of methods have been used to detect spontaneous nocturnal erections for the purpose of distinguishing between organic and psychogenic impotence. In some cases, the patient is placed in an observation room where a nurse visually checks for an erection during the night. This method is both expensive and embarrassing to the patient, producing a strong inhibitory response which can carry over into sleep.

A sophisticated device known as a penile tumescence monitor (PTM) has been used to electronically monitor the thickness of the penis at night during sleep. However the device is very costly (approximately $4500) and of limited availability, causing it to have a substantial inhibiting effect on the patient. It is believed that this inhibition, like that caused by direct observation, can carry over into sleep and prevent spontaneous erection. The PTM also measures only an increase in thickness of the penis, referred to as the phase of "tumescence". It cannot distinguish between a penis which is just tumescent and one that is both tumescent and rigid during erection. Rigidity information is important because a penis will become tumescent prior to erection as a result of blood rushing through it.

Another known method of detecting spontaneous erections is to wrap a strip of postage stamps about the penis to form a continuous ring before going to sleep. A positive indication is obtained if the ring of stamps bursts during sleep. This method relates only to the onset of tumescence and does not indicate whether the penis has become rigid.

Therefore, it is desirable in many applications to provide a technique for detecting and accurately measuring both the degree of tumescence and the grade of rigidity of the penis during spontaneous nocturnal erection.

SUMMARY OF THE INVENTION

The present invention relates to a device for measuring tumescence and rigidity of the penis during erection, comprising: first means receivable about the base of the penis and actuable from an initial condition to an expanded condition by tumescence of the penis; second means mountable to a portion of the penis remote from the base thereof for movement essentially with that portion of the penis; and means for connecting the second means to the first means in a manner permitting movement of the second means away from the first means during erection. In a preferred embodiment, the second means is receivable over the outer end of the penis for movement essentially with the outer end during erection and is actuable from an initial condition to an expanded condition by tumescence of the penis. The first and second means may then include means for restricting return to the initial conditions thereof, and the device may include means for restricting movement of the second means toward the first means. In the same embodiment, the first and second means may include means for progressively increasing resistance of the first and second means to expansion, and the connecting means may include means for progressively increasing resistance of the second means to movement away from the first means.

The device of the present invention is an inexpensive yet highly reliable instrument for detecting and measuring both the degree of tumescence and the grade of rigidity of the penis during nocturnal erection. It can be purchased by a patient for use in the privacy of his home to provide quantitative information as to the occurrence and grade of an erection. The first and second means of the device are preferably ring-like portions receivable over the penis to expand during tumescence. The ring-like portions expand easily and maintain themselves in the expanded condition until the device is manipulated in a specific manner. Similarly, the second ring-like portion can be moved away from the first portion but requires manipulation for movement in the opposite direction. The mechanisms for accomplishing such movements are preferably racheted flexible plastic structures which are inexpensive to manufacture and can be used with a minimum of discomfort.

In use, a patient adjusts the two ring-like portions to fit comfortably about the flaccid penis and draws the second ring-like portion inwardly toward the first portion to coincide with the length of the flaccid penis. He then records the conditions of adjustment of the two ring-like portions and the connecting portion therebetween, preferably by reading markings on the device, and goes to sleep with the device in position on the penis. If the penis undergoes a spontaneous erection during the night, the two ring-like portions will expand to the diameter of the tumescent penis and the second ring-like portion will be moved outwardly to correspond to the length of the erect penis. As the erection subsides, the dimensions of the device will be too great for it to remain in position on the penis, causing the device to fall from the penis during sleep. The patient will find the device in his bed in the morning, at which time he can derive the necessary data from it either by direct measurement or by reading markings on the device. A comparison of the measured data with that obtained when the device was applied permits determinations to be made as to the degree of tumescence and the grade of rigidity obtained during erection. Interpretation of the data can be facilitated by comparison with measurements taken on healthy subjects before and after erection. The measured data can also provide a basis for approximating the pressure of blood achieved within the penis.

The device of the present invention may be designed to progressively increase the resistance of the ring-like portions to expansion and the resistance of the second ring-like portion to outward movement during erection. The device is then able to accurately measure the degree of rigidity achieved during an erection without unduly restricting expansion of the penis at the onset of erection. The device is able to function without waking the patient up and can differentiate between a penis which is just tumescent and one which is both tumescent and highly rigid.

BRIEF DESCRIPTION OF THE DRAWINGS

The above and other features of the present invention may be more fully understood from the following detailed description, taken together with the accompanying drawings, wherein similar reference characters refer to similar elements throughout and in which.

DESCRIPTION OF THE PREFERRED EMBODIMENTS

Figure 1:
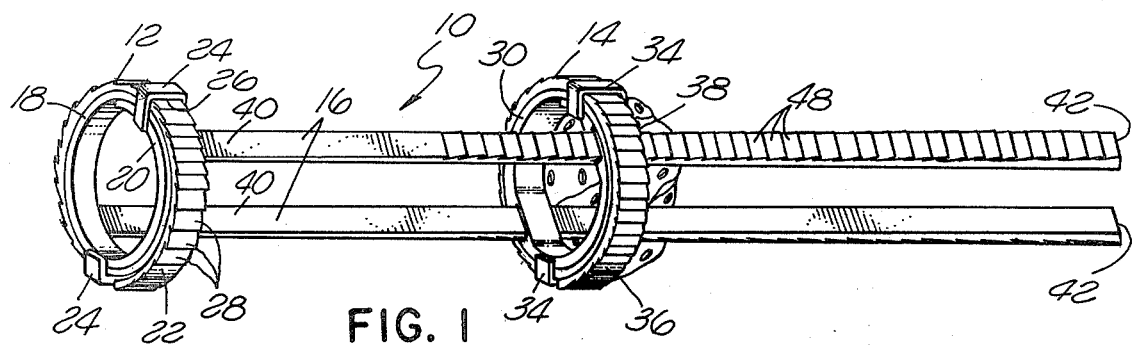
FIG. 1 is a perspective view of the device of the present invention in an initial retracted condition.
Figure 2:
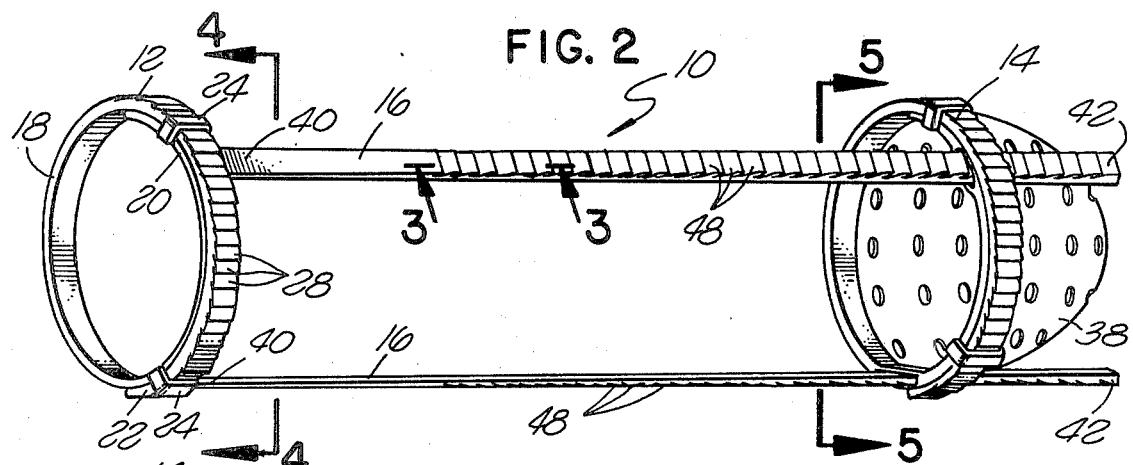
FIG. 2 is a perspective view of the device of FIG. 1 in an expanded condition.

Referring now to the drawings, FIGS. 1 and 2 illustrate a device 10 constructed according to the present invention. The device 10 comprises a first ring-like portion 12 and a second ring-like portion 14 connected by a pair of elongated blade portions 16. The ring-like portions 12 and 14 are designed to be received over the base and the outer end, respectively, of a flaccid penis, and left in that condition overnight to detect spontaneous nocturnal erection of the penis. The device 10 is constructed such that the portions 12 and 14 expand in circumference upon tumescence of the penis, and the portion 14 slides in an outward direction along the blade portions 16 when the penis becomes rigid during erection. The device preferably becomes more resistant to expansion of the portions 12 and 14 and to outward movement of the portion 14 as the penis increases in size. When the erection subsides, the device 10 retains its expanded configuration and tends to fall from the penis without waking up the patient.

Figure 4:
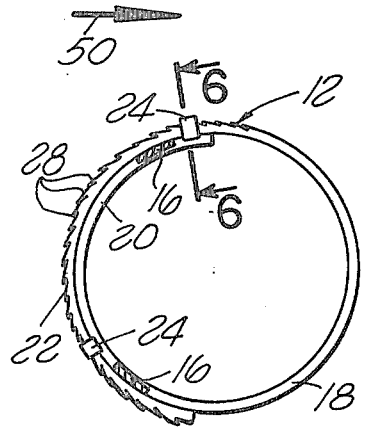
FIG. 4 is a vertical sectional view taken along the line 4—4 of FIG. 2.
Figure 6:
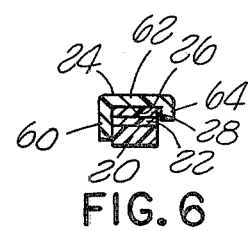
FIG. 6 is a sectional view taken along the line 6—6 of FIG. 4.

With particular reference to FIGS. 4 and 6, the first ring-like portion 12 comprises an elongated segment 18 of flexible material which is wrapped at least partially upon itself in the shape of a ring. The segment 18 extends from a first end portion 20 to a second end portion 22 and carries a pair of guide elements 24 at spaced locations near the first end portion. The shape of the portion 12 is achieved by tucking the second end portion 22 under the guide elements 24 to engage a pair of channels 26 defined by the guide elements and the elongated segment. The second end portion 22 is provided with a plurality of teeth 28 which are constructed to slip past the guide elements 24 when the ring-like portion 12 is expanded, and to engage the guide elements in a ratcheting condition when a contracting force is placed on the portion 12. The ring-like portion 12 is thus readily expanded from the condition of FIG. 1 to the condition of FIG. 2 by tumescence of the penis, but can only be returned to the condition of FIG. 1 by external manipulation of the device.

The thickness of the elongated segment 18 increases along the end portion 22 to progressively increase the resistance of the ring-like portion 12 to expansion forces. Thus, the end portion becomes progressively more confined within the channels 26 as the ring-like portion expands, making it increasingly more difficult to draw each of the teeth 28 through the channels.

Figure 5:
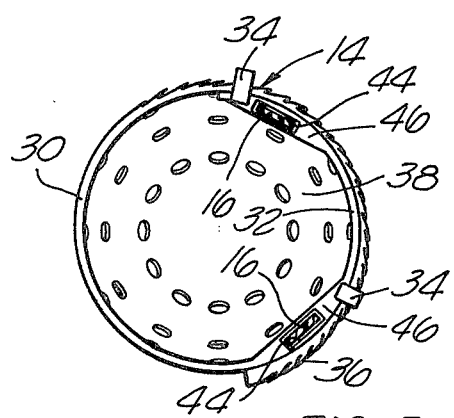
FIG. 5 is a vertical sectional view taken along the line 5—5 of FIG. 2.

The second ring-like portion 14 of FIG. 5 is similar in each of the above-described characteristics to the ring-like portion 12. It has an elongated segment 30 which extends from a first end portion 32 having a pair of guide elements 34 to a second end portion 36. The segment is wrapped at least partially upon itself with the second end portion 36 extending through the guide elements 34 in a racheting relationship. The ring-like portion 14 thus expands with tumescence of the penis and is retracted manually in the same manner as the ring-like portion 12 described above. However, the portion 14 is preferably provided with a sheath 38 attached to one edge of the segment 30 to engage the glans of the penis. The sheath 38 acts in conjunction with the remainder of the portion 14 to securely mount the device 10 to the penis and cause the portion 14 to be carried outwardly during erection.

Each of the blade portions 16 extends from a base 40 to an outer end 42 to provide racheting outward movement of the portion 14 in a manner similar to the racheting expansion of the portions 12 and 14. The bases 40 are carried by the elongated segment 18 of the first ring-like portion 12, preferably at or adjacent to the first end portion 20, and the blade portions extend outwardly through restricted openings 44 of the second ring-like portion 14. The elongated segment 30 may be thickened in the manner shown at 46 to accommodate the openings 44 provided therein. The thickened areas 46 are preferably located at or adjacent to the first end portion 32 of the segment 30 at locations corresponding to the mounting points of the blade portions 16 to the segment 18. The blade portions 16 will then remain parallel to each other as the device expands and contracts.

The blade portions 16 are provided with a plurality of teeth 48 which may be similar to the teeth 28 of the ring-like portions 12 and 14. The teeth 48 are directed toward the outer ends 42 of the blade portions to provide racheting engagement with the restricted openings 44. The ring-like portion 14 is able to slide outwardly along the blade portions 16, but is restricted from movement in the opposite direction by engagement of the teeth 48 with the segment 30. The thickness of the blade portions 16 also increases toward the outer ends 42 to progressively increase resistance to outward movement of the ring-like portion 14. Thus, the device 10 effectively tests the rigidity of the penis during erection.

Figure 3:
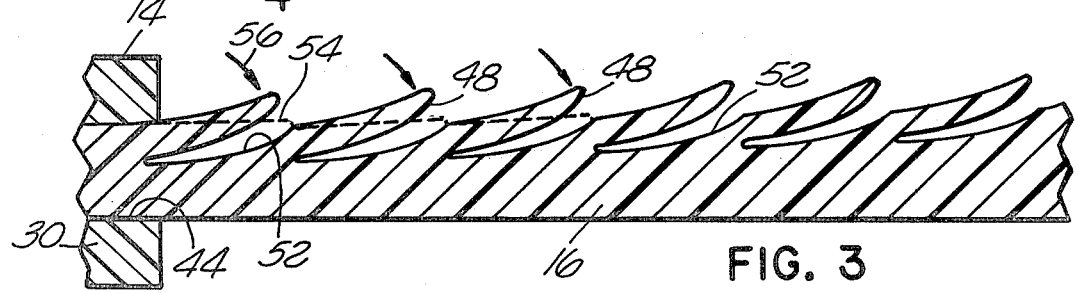
FIG. 3 is an enlarged fragmentary sectional view taken along the line 3—3 of FIG. 2.

The structure of the blade portions 16 can be seen in greater detail in FIG. 3. The teeth 48 of the blade portions permit ratcheting movement of the ring-like portion 14 in the direction indicated at 50, the only limitation on movement in this direction being friction between the increasingly thick blade portion and the opening 44. Each of the teeth 48 overlies a recess 52 such that the ring-like portion 14 can depress the teeth to the broken line condition 54 as it moves in the direction 50. The teeth 48 are preferably formed by making a downward and backward cut into the blade portion 16. The recesses 52 then coincide in size and contour to the undersides of the teeth 48, permitting the teeth to be substantially received within the recesses as the ring-like portion 14 advances outwardly. The teeth 48 normally protrude upwardly to engage the ring-like portion 14 in a manner restricting its inward movement. They must be manually depressed in the direction indicated at 56 before the ring-like portion 14 can be retracted toward the portion 12. The ringlike portion 14 is thus effectively locked in its outermost condition by the teeth 48 following erection, permitting the device to readily fall from the penis for subsequent inspection or measurement.

As seen in FIGS. 4, 5 and 6, the teeth 28 of the elongated segments 18 and 30 may be similar to the teeth of the blade portions 16. Each of the teeth 28 is provided with a corresponding recess 58 into which it can be received during expansion or contraction of the device. Thus, the guide elements 24 of the first ring-like portion 12 act to force the teeth 28 into the recesses during expansion of the portion 12. Retraction of the ring-like portion 12 to the initial condition of FIG. 1 requires manual depression of the teeth 28 to slip them past the guide elements 24.

The structure of the guide element 24 of FIG. 4, and thus the similar guide element 34 of FIG. 5, is seen most clearly in FIG. 6. The guide element has a major leg 60 which is rigidly fixed to the first end portion 20 of the segment 18, and a portion 62 which extends transversly over the end portion 20 to confine the second end portion 22 therebetween. A relatively short depending leg 64 limits transverse movement of the end portion 23. The transverse portion 62 acts as a guide for the second end portion, as a stop element engageable with the teeth 28 to produce racheting, and as a member confining the second end portion to progressively resist expansion of the ring-like portion.

Each element of the device 10, with the possible exception of the guide elements 24 and 26, is preferably made of a suitable resilient material, which may be an organic polymeric material such as polypropylene or polyethylene. The elements will usually be very fine and soft to prevent injury or irritation to the patient.

The device 10 may be provided with suitable markings (not shown) to indicate the extent of expansion of the two ring-like portions and the location of the second ring-like portion 14 along the blade portions 16. Markings will typically be provided on the exterior of the elongated segments 18 and 30 and at least one of the blade portions. The markings may be calibrated to specific thicknesses and lengths of the penis, or be arbitrary markings keyed to a table or chart provided for use with the device 10. In either event, the device 10 must be inspected before and after erection to quantify the degree of tumescence and grade of rigidity achieved during erection. Alternatively, the device can be measured before and after erection. The differences between the two sets of measurements will then indicate the parameters of the erection.

In use, a patient typically purchases the device 10 and applies it to his body when he goes to bed at night. The application process entails manipulation of the ring-like portions 12 and 14 until the device fits comfortably about the base and glans, respectively, of the penis, and adjusting the position of the ring-like portion 14 along the blade portions 16 until the glans is received within the sheath 38. The patient then records the dimensions of the device 10 by either reading its markings or directly measuring it, and goes to sleep with the device in place. A spontaneous erection during the night causes the ring-like portions 12 and 14 to expand to the condition of FIG. 2 and actuates the ring-like portion 14 an appropriate distance along the blade portions. When the erection subsides, the device 10 is too large for the flaccid penis and falls to the side in the patient's bed. The racheting mechanism described above causes the device to maintain the final configuration until intentionally altered by the patient. When the patient wakes up, he measures or takes readings from the device 10 and compares the data with that obtained when the device was applied. The difference indicates the degree of tumescence and grade of rigidity achieved during erection. If, on the other hand, the device remains in the original configuration or increases in diameter without significant movement of the ring-like portion 14 away from the portion 12, the patient knows that a true erection was not achieved. If a negative result is repeated over several attempts, it can be assumed that the patient's sexual impotence is due to an organic disorder.

From the above, it can be seen that the present invention provides an improved apparatus for distinguishing between organic and psychogenically induced sexual impotence. The device is inexpensive and can be used in the privacy of a patient's home, minimizing inhibitions resulting from novelty of the device to the patient or a subconscious feeling that results must be achieved rapidly.

What is claimed is:

1. A device for measuring tumescence and rigidity of the penis during erection comprises:
    first means receivable about the base of the penis and actuable from an initial condition to an expanded condition by tumescence of the penis;
    second means mountable to a portion of the penis remote from the base thereof for movement essentially with said portion of the penis; and
    means for connecting the second means to the first means in a manner permitting movement of the second means away from the first means in response to the erection, said connecting means comprising an elongated element extending outwardly from the first means to the second means alongside the penis.

2. The device of claim 1 wherein the second means is receivable on the penis adjacent to the glans thereof and is actuable from an initial condition to an expanded condition by tumescence of the penis.

3. The device of claim 2 wherein the second means includes a resilient sheath receivable over the glans of the penis.

4. The device recited in claim 1 wherein the first means is marked to visually indicate the extent of tumescence of the penis, and the connecting means is marked to visually indicate the grade of rigidity of the penis during erection.

5. The device of claim 1 wherein the connecting means includes means for progressively increasing resistance of the second means to movement away from the first means.

6. The device recited in claim 1 wherein the connecting means includes means for restricting movement of the second means toward the first means.

7. The device of claim 1 wherein the first means includes means for progressively increasing resistance of the first means to expansion.

8. The device of claim 1 wherein the first means includes means for restricting return of the first means from the expanded condition to the initial condition.

9. The device of claim 1 wherein the first means comprises:
    an elongated segment of flexible material having first and second end portions wrapped at least partially upon each other in the shape of a ring;
    a guide element carried with the first end portion and extending transversely relative to the segment to define a channel receiving the second end portion for sliding movement between the initial and expanded conditions of the first means; and a plurality of tooth means carried by the second end portion and engaging the guide element to restrict return of the first means from the expanded condition to the initial condition.

10. The device of claim 9 wherein the tooth means are constructed and arranged in a manner permitting them to be depressed for contraction of the first means toward the initial condition.

11. The device of claim 9 wherein the second end portion of the elongated segment increases in thickness in a direction away from the first end portion to progressively increase the resistance of the first means to expansion.

12. A device for measuring tumescence and rigidity of the penis during erection comprises:

first means receivable about the base of the penis and actuable from an initial condition to an expanded condition by tumescence of the penis;

second means mountable to a portion of the penis remote from the base thereof for movement essentially with said portion of the penis; and means for connecting the second means to the first means in a manner permitting movement of the second means away from the first means during erection;

said connecting means comprising at least one elongated element extending outwardly from the first means and received within a restricted opening of the second means; and said elongated element having a plurality of tooth means which engage the second means in a manner permitting movement of the second means away from the first means and restricting movement of the second means toward the first means.

13. The device of claim 12 wherein the tooth means are constructed and arranged in a manner permitting them to be depressed for movement of the second means toward the first means.

14. The device of claim 12 wherein the elongated element increases in thickness in a direction away from the first means to progressively increase the resistance to movement of the second means away from the first means.

15. A device for measuring tumescence and rigidity of the penis during erection comprises:

first means receivable about the base of the penis and actuable from an initial condition to an expanded condition by tumescence of the penis;

second means mountable to a portion of the penis remote from the base thereof for movement essentially with said portion of the penis; and means for connecting the second means to the first means in a manner permitting movement of the second means away from the first means during erection;

said first means comprising an elongated segment of flexible material wrapped at least partially upon itself in the shape of a ring and having stop means thereon, and a plurality of teeth carried by the elongated segment and engaging the stop means to restrict return of the first means from the expanded condition to the initial condition.

16. A device for measuring tumescence and rigidity of the penis during erection comprises:

first means receivable about the base of the penis and actuable from an initial condition to an expanded condition by tumescence of the penis;

second means receivable over the outer end of the penis for movement essentially with said outer end during erection and actuable from an initial condition to an expanded condition by tumescence of the penis;

the first and second means including means for restricting return to the initial conditions thereof;

means for connecting the second means to the first means in a manner permitting movement of the second means away from the first means during erection; and means for restricting movement of the second means toward the first means.

17. The device of claim 16 wherein the first and second means include means for progressively increasing resistance thereof to expansion, and the connecting means includes means for progressively increasing resistance of the second means to movement away from the first means.

18. The device of claim 17 wherein the first means comprises:

an elongated segment of flexible material having first and second end portions wrapped at least partially upon each other in the shape of a ring;

a guide element carried with the first end portion and extending transversely relative to the segment to define a channel receiving the second end portion for sliding movement between the initial and expanded conditions of the first means; and a plurality of tooth means carried by the second end portion and engaging the guide element to restrict return of the first means from the expanded condition to the initial condition.

19. The device of claim 18 wherein the connecting means comprises at least one elongated element extending outwardly from the first means and received within a restricted opening of the second means, the elongated element having a plurality of tooth means which engage the second means in a manner permitting movement of the second means away from the first means and restricting movement of the second means toward the first means.

* * * * *